United States Patent
Tobe et al.

[11] Patent Number: 5,869,536
[45] Date of Patent: *Feb. 9, 1999

[54] TREATMENT OF HYPERKINETIC DISORDERS

[75] Inventors: Akihiro Tobe; Tadashi Tanaka; Tomoko Tamura, all of Tokyo, Japan

[73] Assignee: Mitsubishi Chemical Corporation, Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 500,788

[22] Filed: Jul. 11, 1995

[30] Foreign Application Priority Data

Jul. 12, 1994 [JP] Japan .................................. 6-159866

[51] Int. Cl.⁶ .............................................. A61K 31/135
[52] U.S. Cl. ............................................ 514/648
[58] Field of Search ................................. 514/648

[56] References Cited

U.S. PATENT DOCUMENTS

| | | | |
|---|---|---|---|
| 4,024,282 | 5/1977 | Kikumoto et al. | 424/330 |
| 4,060,641 | 11/1977 | Kikumoto et al. | 424/330 |
| 4,071,559 | 1/1978 | Kikumoto et al. | 424/330 |
| 4,507,322 | 3/1985 | Kuriyama et al. | 514/648 |

FOREIGN PATENT DOCUMENTS 1 512 880  6/1978  United Kingdom .

OTHER PUBLICATIONS

Nomura, Pharmacology Biochemistry and Behaviour, vol. 42, Nov. 4, 1992 pp. 721–731.

Fox et al, Drug Safety, vol. 9, Nov. 1, 1993, pp. 38–50.

Meller et al., Primary Care, vol. 14, Nov. 4, 1987, pp. 745–758.

Medline Abstract #92383279, Nomura, "Effects of bifemline on discrimination learning of serotmergy–dysfunction rats", *pharmacol. Biochm. Behav;* 42(4) pp. 721–731 Aug. 1992.

Medline Abstract 88203861, Gold et al, "Methyseigid Penetrates the hyproactivity produced by MDMA in rats", *Pharmacol Biochem. Behav* (Mar. 1988), 29(3), 645–648.

*Primary Examiner*—Keith D. MacMillan
*Attorney, Agent, or Firm*—Wenderoth, Lind & Ponack, L.L.P.

[57] ABSTRACT

A pharmaceutical composition for treating hyperkinetic disorders, which contains as an active ingredient an effective amount of 2-(4-methylamino butoxy)diphenylmethane, is provided. A method of treating hyperkinetic disorders with said pharmaceutical composition and use of said diphenylmethane for preparing said composition are also provided.

3 Claims, No Drawings

TREATMENT OF HYPERKINETIC DISORDERS

The present invention relates to the treatment of hyperkinetic disorders, an important pediatric disease. In particular, it relates to a pharmaceutical composition for treating hyperkinetic disorders, which contains as an essential component an effective amount of 2-(4-methylaminobutoxy)diphenylmethane together with a suitable carrier therefor, a method of treating hyperkinetic disorders by administering said compound to patients suffering from said disorder, and use of the compound for preparing the pharmaceutical composition mentioned above.

Hyperkinetic disorders, which is also called as aprosexia or hyperkinetic obstacles, is one of the important pediatric diseases. This disease is characterized by accompanying three symptoms, namely marked inattention, hyperactivity and impulsivesness and distinguished from pervasive developmental disorder such as autism, maniac-depressive psychosis and anxiety disorders.

A lot of causes have been proposed for hyperkinetic disorders such as encephalopathy in perinatal period, inheritance, central norepinephrine disorder, lead poisoning or the like. However, the real causes have not yet been determined. There is an inclination that this disease is found in infants at age not more than 6 and that hyperactivity itself, pathological aspect of the disease, calms with the progress of age. However, since there often remain problems such as juvenile delinquency for a long time, it is necessary to make sufficient treatment at an early stage.

A growing therapeutic method has heretofore been adopted for treating this disease. Namely, patients have been given training so as to engage in appropriate social life together with psychotherapy, behavior therapy, sensor integration therapy or the like. Further, physicians sometimes make experimental or tentative drug therapy with drugs which have not been given a governmental approval to be applied for hyperkinetic disorders. However, it is uncertain that these drugs are effective for treating hyperkinetic disorders, and also, they have problems such as strong side effects.

One object of the present invention is to provide a new medicine which is effective for treating hyperkinetic disorders with reduced side effects. Another object of the present invention is to provide a method of treating hyperkinetic disorders by administering the medicine to patients suffering from the disorder. Additional objects of the present invention will be apparent from the subsequent description.

The present inventors have found that 2-(4-methylaminobutoxy)-diphenylmethane, which is disclosed in Japanese Patent Publication (Kokoku) No. Hei 60-6349 specification, is useful for treating infantile hyperkinetic disorders. The present invention has been established based on such finding.

It is reported in GB 1512880 publication that 2-(4-methylaminobutoxy)-diphenylmethane possesses an antidepressant activity, and it is also known from EP 103897 publication that this compound is useful as an agent for improving and treating pathergasia caused by intracranial organic disease such as cerebral hemorrhage or the like. A medicine containing 2-(4-methylaminobutoxy) diphenylmethane hydrochloride as an effective ingredient, which has a generic name of "bifelane hydrochloride", is commercially available and has been used for improving cerebral nerve function, in particular, for treating aftereffect of cerebral occlusion or hemorrhage accompanied by volition lowering and emotional disorder.

According to the present invention, a pharmaceutical composition for treating hyperkinetic disorders, which contains as an essential component 2-(4-methylaminobutoxy) diphenylmethane of the formula (1):

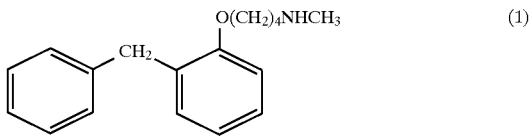

or a hydrate or pharmaceutically acceptable salt thereof, is provided.

The hyperkinetic disorders, for the treatment of which the pharmaceutical composition of the invention is applied, is defined as follows:

After considering the infantile age and development stage, the following points (1) and (2) are observed in addition to aprosexia, activity disorder and impulsive insanity.

(1) Of the following 5 symptoms of aprosexia, at least 3 should be observed:
(a) the infant shows no durable voluntary activity, (b) the infant very often leaves playing unfinished, (c) the infant changes its activity one after another, (d) the infant markedly lacks persistency for work instructed by an adult, and (e) the infant fails to concentrate its attention upon studying such as homework and reading as instructed.

(2) In addition, at least 2 of 4 symptoms of activity disorder mentioned below should be observed:
(a) under inappropriate conditions the infant shows a restless appearance, inclusive of always and excessively running about and, in particular, climbing up, (b) the infant is excessively restless and fidgety during spontaneous activity, (c) the infant shows particularly excessive movements under conditions requiring calmness such as dinner, during the making a trip or visit, at church, and (d) the infant very often leaves its seat in a classroom or in other situations requiring it to remain seated.

In addition to the diagnostic criteria stated above, the following should be considered:

(3) abnormal attentiveness and activity are observed in school or kindergarten, or during seeing a doctor;

(4) the diagnostic criteria on the pervasive developmental disorders, mood disorders such as mania or depression, or anxiety disorders are not sufficed;

(5) hyperkinetic disorders onsets at age not more than 6 years and continues for at least 6 months; and (6) the infant has IQ not less than 50.

The compound of the formula (1) can be easily prepared according to the method as described, for example, in Japanese Patent Publication (Kokoku) No. Sho 60-6349 specification (Example 1) or Japanese Patent Publication (Kokoku) No. Hei 2-33689 (Column 4–5). A free form of said compound, its hydrate or a physiologically acceptable acid addition salt thereof may be used as an active ingredient of the pharmaceutical composition of the present invention.

The pharmacologically acceptable acid addition salts include mineral acid salts such as hydrochloride, hydrobromide, hydroiodide, sulfate, nitrate and phosphate; or organic acid salts such as acetate, maleate, fumarate, citrate, oxalate, succinate, tartarate, malate, mandelate, methanesulfonate, p-toluenesulfonate and 10-camphor sulfonate, with the hydrochloride of said compound being preferred. The hydrochloride is commercially available as a substance having the generic name "bifemelane hydrochloride".

Route of administration of the pharmaceutical composition is not particularly limited, and it may be administered by oral and parenteral routes, with oral administration being preferred. The compound of the formula (1) may be used alone for treating said disorder, but ordinarily, a conventional pharmaceutical formulation comprising the compound of the formula (1) together with pharmacologically and pharmaceutically acceptable additives may be prepared. The pharmacologically and pharmaceutically acceptable additives include, for example, excipients, disintegrators or disintegration aids, binders, lubricants, coating agents, pigments, diluents, bases, dissolving agents or solubilizers, isotonic agents, pH regulators, stabilizers, propellants, adhesives, and the like.

Appropriate formulations for oral administration include, for example, tablets, capsules, powders, fine granules, granules, solutions, syrups and the like. Appropriate formulations for parenteral administration include, for example, injections, drops, suppositories, inhalants, plasters, and the like.

The formulations suitable for oral, percutaneous or transmucosal administration may contain pharmaceutically acceptable additives including excipients such as glucose, lactose, D-mannitol, starch or crystalline cellulose; disintegrators or disintegration aids such as carboxymethyl cellulose, starch or calcium carboxymethyl cellulose, etc.; binders such as hydroxypropyl cellulose, hydroxypropyl methyl cellulose, polyvinylpyrrolidone or gelatin; lubricants such as magnesium stearate or talc; coating agents such as hydroxypropyl methyl cellulose, saccharose, polyethylene glycol or titanium oxide; and bases such as vaseline, liquid paraffin, polyethylene glycol, gelatin, kaolin, glycerin, purified water or hard fat. Further, such formulations may be prepared by adding pharmaceutical additives including propellants such as fron, diethyl ether or compressed gas; adhesives such as sodium polyacrylate, polyvinyl alcohol, methyl cellulose, polyisobutylene or polybutene; basic cloth such as cotton cloth or plastic sheet; and the like.

The formulations appropriate for injection or drip infusion may contain pharmaceutical additives including dissolving agents or dissolution aids which can form aqueous injections or those of the dissolving type-in use such as distilled water for injection, physiological brine or propylene glycol; isotonic agents such as glucose, sodium chloride, D-mannitol or glycerin; pH regulators such as inorganic acids, organic acids, inorganic bases or organic bases; and the like.

Pharmaceutical formulations for treating cerebral nerve function which contain the compound of the formula (1) as an active ingredient are already commercially available under the generic name "bifemelane hydrochloride" and trade names "Alnert" and "Celeport" by Fujisawa Pharmaceutical Chemical Industries, Co., Ltd. and Eisai Co., Ltd., respectively. Said commercially available formulations may be used as a pharmaceutical composition of the present invention for treating hyperkinetic disorders.

Appropriate dosage of said composition is not limitative and can be appropriately determined depending upon administering route, age or body weight of patients, symptoms of the disease, and the like. For example, for oral administration, the daily dosage for adult, which corresponds to about 5–300 mg, preferably about 50–200 mg, particularly preferably 150 mg of the active ingredient can be used as a basis for calculating the daily dosage for infants. The pharmaceutical composition of the present invention may be administered once a day or several times at devided daily dose, and the period of administration may be appropriately determined, depending upon the age of particular infant and degree of the symptoms. Further, 2-(4-methylaminobutoxy)diphenylmethane incorporated into the composition of the present invention is almost nontoxic as will be noted from the acute toxicity value listed in Table 1 of Japanese Patent Publication (Kokoku) No. Hei 2- 33689 specification. Since the pharmaceutical composition is aimed at application to infants, it may be easily understood that such characteristics of said composition is very advantageous to this invention.

EXAMPLE

Pharmaceutical formulations of the present invention are shown below, but the formulations of the present invention are not limited to those examples.

Formulation 1

2-(4-Methylaminobutoxy)diphenylmethane hydrochloride 100 g

Mannit 300 g

Corn starch 450 g

Lactose 300 g

Hydroxypropyl cellulose 38 g

Calcium stearate 12 g

The above ingredients are admixed in a conventional manner to give capsules weighing 120 mg per capsule.

Formulation 2

2-(4-Methylaminobutoxy)diphenylmethane hydrochloride 100 g

Corn starch 200 g

Lactose 500 g

Calcium carboxymethyl cellulose 150 g

Polyvinylpyrrolidone 75 g

Talc 75 g

Microcrystalline cellulose 250 g

The above ingredients are admixed in a conventional manner and granulated and subjected to a tableting machine to give tablets weighing 120 mg per tablet.

Formulation 3

2-(4-Methylaminobutoxy)diphenylmethane hydrochloride 50 mg

Hydroxypropyl cellulose 4 mg

Hydroxypropylmethyl cellulose 50 mg

Sodium citrate 50 mg

Sodium saccharin 3 mg

Saccharose optimum dose

Corn starch 29 mg

D-Mannitol 67 mg

Glycerin monostearate 200 mg

Eudragit L-30D55 71 mg

Macrogoal 6000 7 mg

Talc 21 mg

Sodium laurylsulfate trace

Perfume trace 1000 mg

The above ingredients are admixed in a conventional manner to give dry syrup.

Formulation 4

2-(4-Methylaminobutoxy)diphenylmethane hydrochloride 50 mg

Hydroxypropyl cellulose 70 mg

Corn starch 50 mg

D-Mannitol optimum dose

Aminoalkyl methacrylate copolymer E 85 mg

Talc 60 mg

Calcium stearate 5 mg 1000 mg

The above ingredients are admixed to give granules.

Clinical Tests

Bifemelane hydrochloride was administered to 3 patients diagnosed as having hyperkinetic disorders over 12 weeks at a dose of 3–6 mg/kg/day.

Case 1.

A male infant aged 10 years 11 months with an IQ 85 had an abnormal; maternity history inclusive of low body weight and serious jaudice at birth due to being a twin. The patient complained of hyperactivity, emotional disorder and inhouse violence, and its general severity was regarded as "very serious". After treatment with the pharmaceutical composition of the invention for 12 weeks, the severity of disease turned to "slight disorder". Although aggressive and restless aspects still remained slightly, the hyperactivity and emotional instability disappeared. Soon after initiating the administration of the composition, he complained of headache for 2 days, but the symptom was slight and disappeared without treatment. The attending doctor decided that the composition is "useful".

Case 2

A male infant with IQ 51, aged 5 months and 6 years, was born 5 weeks prematurely in a state of suspended animation with serious jaudice. He complained of hyperactivity, difficulty of concentration, impulsiveness, insomnia and an inclination of excessive awakeness. Its general severity was considered "very serious". After treatment with the composition for 12 weeks, the severity of disease turned to "slight". In particular, remarkable effect was shown on the hyperactivity and restlessness.

Case 3.

A male infant with IQ60–70, aged 6 months and 4 years had no particular abnormal aspect during pregnancy and at birth. The patient complained that he cannot speak well, with hyperactivity and restlessness being observed. In particular, hyperactivity and restlessness were serious. The general severity turned from "serious" to "slight" after treatment with the composition for 4 weeks, and the surrounding symptoms such as emotional instability, awkwardness or the like were also improved before the treatment of 12 weeks is finished. Further, he has begun to positively contact his kindergarten's teachers, friends, and grandmother.

EFFECT OF THE INVENTION

The pharmaceutical composition of the present invention is highly effective in treating hyperkinetic disorders and relieving the symptoms, and yet, it has negligible toxicity, and therefore, the composition of the invention is useful for treating hyperkinetic disorders of infants.

What is claimed is:

1. A method of treating hyperkinetic disorders which comprises administering an effective amount of 2-(4-methylaminobutoxy)-diphenylmethane or a hydrate or pharmaceutically acceptable salt thereof to a patient in need of such treatment.

2. The method of claim 1, wherein the patient has at least three of the following symptoms:
   a) shows no durable voluntary activity;
   b) often leaves playing unfinished;
   c) changes activity one after another;
   d) lacks persistency for work instructed by another; and
   e) fails to concentrate attention.

3. The method of claim 2, wherein the patient additionally has at least two of the following symptoms:
   a) demonstrates a restless appearance;
   b) excessive restless and fidgeting during spontaneous activity;
   c) shows excessive movement under conditions requiring calmness; and
   d) often leaves seat in conditions requiring one to remain seated.

* * * * *